US009463805B2

(12) United States Patent
Kirsch et al.

(10) Patent No.: US 9,463,805 B2
(45) Date of Patent: Oct. 11, 2016

(54) SYSTEM AND METHOD FOR DYNAMIC VEHICLE CONTROL AFFECTING SLEEP STATES OF VEHICLE OCCUPANTS (71) Applicant: Honda Motor Co., Ltd., Tokyo (JP)

(72) Inventors: David M. Kirsch, Torrance, CA (US); Harinkumar Vashi, Los Angeles, CA (US); Bonnie Chen, Torrance, CA (US)

(73) Assignee: Honda Motor Co., Ltd., Tokyo (JP)

( * ) Notice: Subject to any disclaimer, the term of this patent is extended or adjusted under 35 U.S.C. 154(b) by 92 days.

(21) Appl. No.: 14/573,642

(22) Filed: Dec. 17, 2014

(65) Prior Publication Data
US 2016/0176409 A1    Jun. 23, 2016

(51) Int. Cl.
| B60W 40/08 | (2012.01) |
| B60G 17/015 | (2006.01) |
| B60N 2/44 | (2006.01) |
| A61B 5/18 | (2006.01) |
| A61B 5/00 | (2006.01) |
| A61M 21/02 | (2006.01) |
| A61M 21/00 | (2006.01) |

(52) U.S. Cl.
CPC ............... *B60W 40/08* (2013.01); *A61B 5/18* (2013.01); *A61B 5/4812* (2013.01); *A61B 5/6801* (2013.01); *A61B 5/6893* (2013.01); *A61B 5/6898* (2013.01); *A61M 21/02* (2013.01); *B60G 17/015* (2013.01); *B60N 2/442* (2013.01); *A61M 2021/0022* (2013.01); *A61M 2205/3303* (2013.01); *A61M 2205/3584* (2013.01); *A61M 2205/502* (2013.01); *A61M 2205/52* (2013.01); *B60G 2400/96* (2013.01); *B60W 2040/0818* (2013.01); *B60W 2040/0827* (2013.01); *B60W 2040/0872* (2013.01); *B60W 2540/22* (2013.01); *B60W 2540/26* (2013.01)

(58) Field of Classification Search
CPC ............................. G06G 7/48; B60R 16/037
See application file for complete search history.

(56) References Cited

U.S. PATENT DOCUMENTS

| 6,265,978 | B1 | 7/2001 | Atlas | |
| 8,781,568 | B2 | 7/2014 | Dugan et al. | |
| 9,082,239 | B2 * | 7/2015 | Ricci | B60Q 1/00 |
| 2009/0312998 | A1 * | 12/2009 | Berckmans | G06F 19/3437 |
| | | | | 703/11 |
| 2010/0268051 | A1 | 10/2010 | Prasad et al. | |
| 2011/0244919 | A1 * | 10/2011 | Aller | G06K 9/00973 |
| | | | | 455/556.1 |
| 2014/0059066 | A1 | 2/2014 | Koloskov | |
| 2014/0309891 | A1 * | 10/2014 | Ricci | H04W 48/04 |
| | | | | 701/48 |
| 2015/0126845 | A1 * | 5/2015 | Jin | A61B 5/726 |
| | | | | 600/383 |

* cited by examiner

*Primary Examiner* — Thomas Tarcza
*Assistant Examiner* — Alex C Dunn
(74) *Attorney, Agent, or Firm* — Rankin, Hill & Clark LLP (57) ABSTRACT A computer-implemented method for dynamic vehicle control affecting sleep states of vehicle occupants includes connecting a wearable computing device associated with a vehicle occupant to a vehicle, and determining a state of the vehicle occupant based on physiological data received from at least one of the wearable computing device and the vehicle. The method includes determining a target sleep state of the vehicle occupant based on at least one of the state of the vehicle occupant, the physiological data and vehicle system data, and controlling a vehicle system of the vehicle based on the state of the vehicle occupant in relation to the target sleep state. The method includes monitoring the state of the vehicle occupant including monitoring the physiological data of the vehicle occupant in response to controlling the vehicle system and controlling the vehicle system according to the monitoring in relation to the target sleep state.

20 Claims, 4 Drawing Sheets

SYSTEM AND METHOD FOR DYNAMIC VEHICLE CONTROL AFFECTING SLEEP STATES OF VEHICLE OCCUPANTS

BACKGROUND

Wearable technologies and other portable computing devices can be integrated across different domains and fields for data acquisition on aspects of a user's daily life. In particular, wearable technologies including wearable sensors can monitor and assess biometric data, user states, user activity, user motion, sleep cycles, and other inputs a user encounters on a daily basis.

Within a vehicle context, data from wearable technologies can be used, in part, to determine states and behaviors of vehicle occupants. Data related to sleep states can provide knowledge on vehicle occupant fatigue in a vehicle. A dynamic and contextual vehicle can provide a pleasant and safe driving experience for the vehicle occupants by adapting vehicle systems in real time for particular driving situations and sleep states of the vehicle occupants.

BRIEF DESCRIPTION

According to one aspect, a computer-implemented method for dynamic vehicle control affecting sleep states of vehicle occupants, includes connecting a wearable computing device associated with a vehicle occupant to a vehicle and determining a state of the vehicle occupant based on physiological data received from at least one of the wearable computing device and the vehicle. The method includes determining a target sleep state of the vehicle occupant based on at least one of the state of the vehicle occupant, the physiological data and vehicle system data and controlling a vehicle system of the vehicle based on the state of the vehicle occupant in relation to the target sleep state. The method includes monitoring the state of the vehicle occupant including monitoring the physiological data of the vehicle occupant in response to controlling the vehicle system and controlling the vehicle system according to the monitoring in relation to the target sleep state.

According to another aspect, a system for dynamic vehicle control affecting sleep states of vehicle occupants, includes a wearable computing device associated with a vehicle occupant, and a vehicle including a vehicle system, vehicle sensors and a processor, the processor operably connected for computer communication to the wearable computing device. The system includes a state determination module of the processor to determine a state of the vehicle occupant based on physiological data received from at least one of the wearable computing device and the vehicle. The state determination module also determines a target sleep state of the vehicle occupant based on at least one of the state of the vehicle occupant, the physiological data and vehicle system data. The system includes a vehicle control module of the processor to control the vehicle system based on the state of the vehicle occupant in relation to the target sleep state. The system includes a state monitoring module of the processor to monitor the state of the vehicle occupant including monitoring the physiological data of the vehicle occupant in response to controlling the vehicle system. Further, the vehicle control module controls the vehicle system according to the monitoring in relation to the target sleep state.

According to a further aspect, a non-transitory computer-readable storage medium storing instructions that, when executed by a computer, causes the computer to perform a method. The method includes connecting a wearable computing device associated with a vehicle occupant to a vehicle and receiving physiological data associated with the vehicle occupant from at least one of the wearable computing device and the vehicle. The method also includes receiving vehicle system data from the vehicle. Further, the method includes determining a state of the vehicle occupant based on the physiological data and determining a target sleep state based on at least one of the state of the vehicle occupant, the physiological data and vehicle system data. The method includes transmitting a vehicle control command to a vehicle system of the vehicle based on the state of the vehicle occupant in relation to the target sleep state. The method includes monitoring the physiological data of the vehicle occupant in response to controlling the vehicle system and transmitting a second vehicle control command to the vehicle system in response to the monitoring, the second vehicle control command based on the monitoring in relation to the target sleep state.

DETAILED DESCRIPTION

The following includes definitions of selected terms employed herein. The definitions include various examples and/or forms of components that fall within the scope of a term and that can be used for implementation. The examples are not intended to be limiting.

A "bus", as used herein, refers to an interconnected architecture that is operably connected to other computer components inside a computer or between computers. The bus can transfer data between the computer components. The bus can be a memory bus, a memory controller, a peripheral bus, an external bus, a crossbar switch, and/or a local bus, among others. The bus can also be a vehicle bus that interconnects components inside a vehicle using protocols such as Media Oriented Systems Transport (MOST), Controller Area network (CAN), Local Interconnect Network (LIN), among others.

"Computer communication", as used herein, refers to a communication between two or more computing devices (e.g., computer, personal digital assistant, cellular telephone, network device) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, among others.

A "disk", as used herein can be, for example, a magnetic disk drive, a solid state disk drive, a floppy disk drive, a tape drive, a Zip drive, a flash memory card, and/or a memory stick. Furthermore, the disk can be a CD-ROM (compact disk ROM), a CD recordable drive (CD-R drive), a CD rewritable drive (CD-RW drive), and/or a digital video ROM drive (DVD ROM). The disk can store an operating system that controls or allocates resources of a computing device.

A "database", as used herein can refer to table, a set of tables, a set of data stores and/or methods for accessing and/or manipulating those data stores. Some databases can be incorporated with a disk as defined above.

A "memory", as used herein can include volatile memory and/or non-volatile memory. Non-volatile memory can include, for example, ROM (read only memory), PROM (programmable read only memory), EPROM (erasable PROM), and EEPROM (electrically erasable PROM). Volatile memory can include, for example, RAM (random access memory), synchronous RAM (SRAM), dynamic RAM (DRAM), synchronous DRAM (SDRAM), double data rate SDRAM (DDR SDRAM), and direct RAM bus RAM (DRRAM). The memory can store an operating system that controls or allocates resources of a computing device.

A "module", as used herein, includes, but is not limited to, non-transitory computer readable medium that stores instructions, instructions in execution on a machine, hardware, firmware, software in execution on a machine, and/or combinations of each to perform a function(s) or an action(s), and/or to cause a function or action from another module, method, and/or system. A module may also include logic, a software controlled microprocessor, a discrete logic circuit, an analog circuit, a digital circuit, a programmed logic device, a memory device containing executing instructions, logic gates, a combination of gates, and/or other circuit components. Multiple modules may be combined into one module and single modules may be distributed among multiple modules.

An "operable connection", or a connection by which entities are "operably connected", is one in which signals, physical communications, and/or logical communications can be sent and/or received. An operable connection can include a wireless interface, a physical interface, a data interface and/or an electrical interface.

A "processor", as used herein, processes signals and performs general computing and arithmetic functions. Signals processed by the processor can include digital signals, data signals, computer instructions, processor instructions, messages, a bit, a bit stream, or other means that can be received, transmitted and/or detected. Generally, the processor can be a variety of various processors including multiple single and multicore processors and co-processors and other multiple single and multicore processor and co-processor architectures. The processor can include various modules to execute various functions.

A "portable device", as used herein, is a computing device typically having a display screen with user input (e.g., touch, keyboard) and a processor for computing. Portable devices include, but are not limited to, handheld devices, mobile devices, smart phones, laptops, tablets and e-readers. In some embodiments, a "portable device" could refer to a remote device that includes a processor for computing and/or a communication interface for receiving and transmitting data remotely.

A "vehicle", as used herein, refers to any moving vehicle that is capable of carrying one or more human occupants and is powered by any form of energy. The term "vehicle" includes, but is not limited to: cars, trucks, vans, minivans, SUVs, motorcycles, scooters, boats, go-karts, amusement ride cars, rail transport, personal watercraft, and aircraft. In some cases, a motor vehicle includes one or more engines. Further, the term "vehicle" can refer to an electric vehicle (EV) that is capable of carrying one or more human occupants and is powered entirely or partially by one or more electric motors powered by an electric battery. The EV can include battery electric vehicles (BEV) and plug-in hybrid electric vehicles (PHEV). The term "vehicle" can also refer to an autonomous vehicle and/or self-driving vehicle powered by any form of energy. The autonomous vehicle may or may not carry one or more human occupants. Further, the term "vehicle" can include vehicles that are automated or non-automated with pre-determined paths or free-moving vehicles.

A "vehicle system", as used herein can include, but is not limited to, any automatic or manual systems that can be used to enhance the vehicle, driving and/or safety. Exemplary vehicle systems include, but are not limited to: an electronic stability control system, an anti-lock brake system, a brake assist system, an automatic brake prefill system, a low speed follow system, a cruise control system, a collision warning system, a collision mitigation braking system, an auto cruise control system, a lane departure warning system, a blind spot indicator system, a lane keep assist system, a navigation system, a transmission system, brake pedal systems, an electronic power steering system, visual devices (e.g., camera systems, proximity sensor systems), a climate control system, an electronic pretensioning system, a monitoring system, a passenger detection system, a vehicle suspension system, a vehicle seat configuration system, a vehicle cabin lighting system, an audio system, a sensory system, among others.

A "vehicle occupant", as used herein can include, but is not limited to, one or more biological beings located in the vehicle. The vehicle occupant can be a driver or a passenger of the vehicle. The vehicle occupant can be a human (e.g., an adult, a child, an infant) or an animal (e.g., a pet, a dog, a cat).

A "wearable computing device", as used herein can include, but is not limited to, a computing device component (e.g., a processor) with circuitry that can be worn or attached to user. In other words, a wearable computing device is a computer that is subsumed into the personal space of a user. Wearable computing devices can include a display and can include various sensors for sensing and determining various parameters of a user. For example, location, motion, and physiological parameters, among others. Some wearable computing devices have user input and output functionality. Exemplary wearable computing devices can include, but are not limited to, watches, glasses, clothing, gloves, hats, shirts, jewelry, rings, earrings necklaces, armbands, shoes, earbuds, headphones, personal wellness devices, collars, and leashes.

I. System Overview

Figure 1:
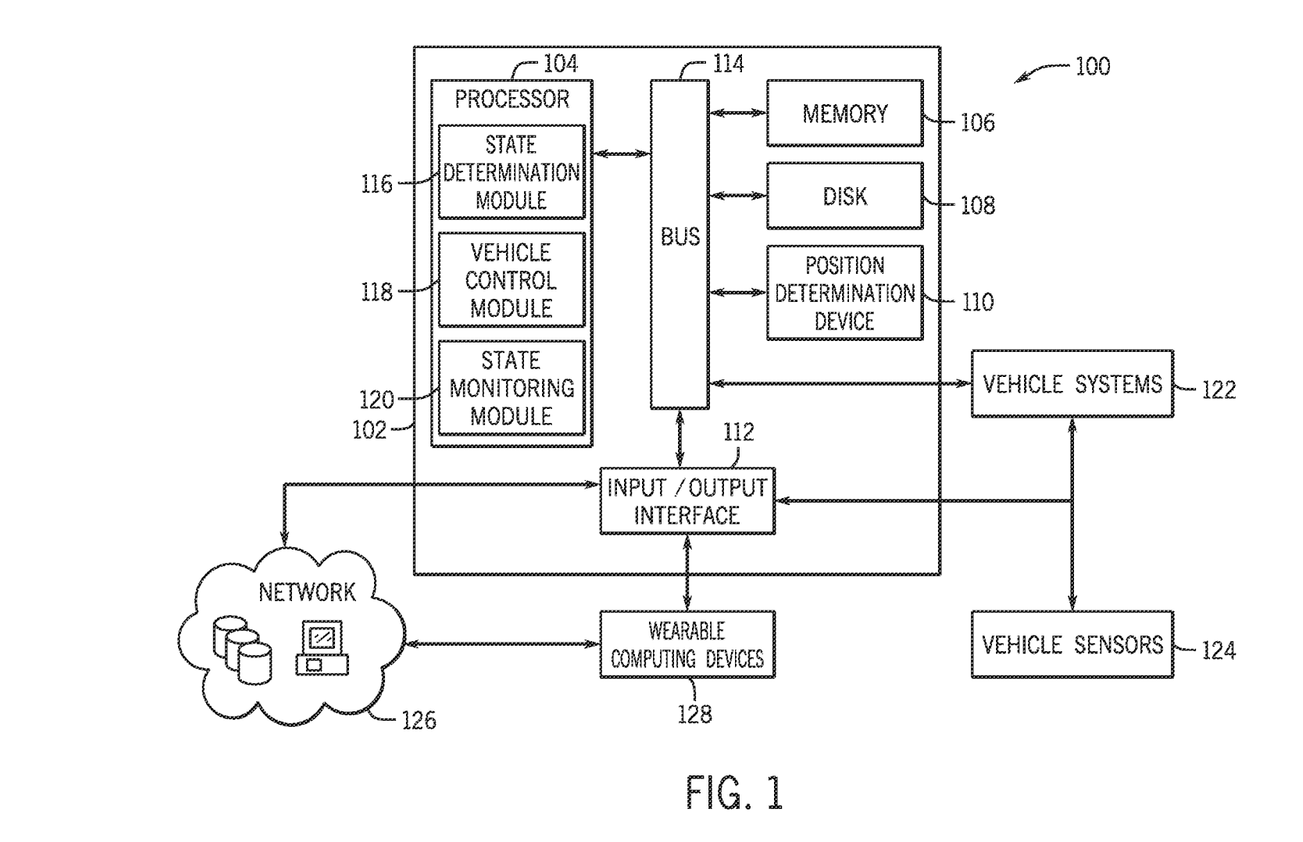
FIG. 1 is a schematic diagram of an operating environment for implementing systems and methods for dynamic vehicle control affecting sleep states of vehicle occupants according to an exemplary embodiment.
Figure 3:
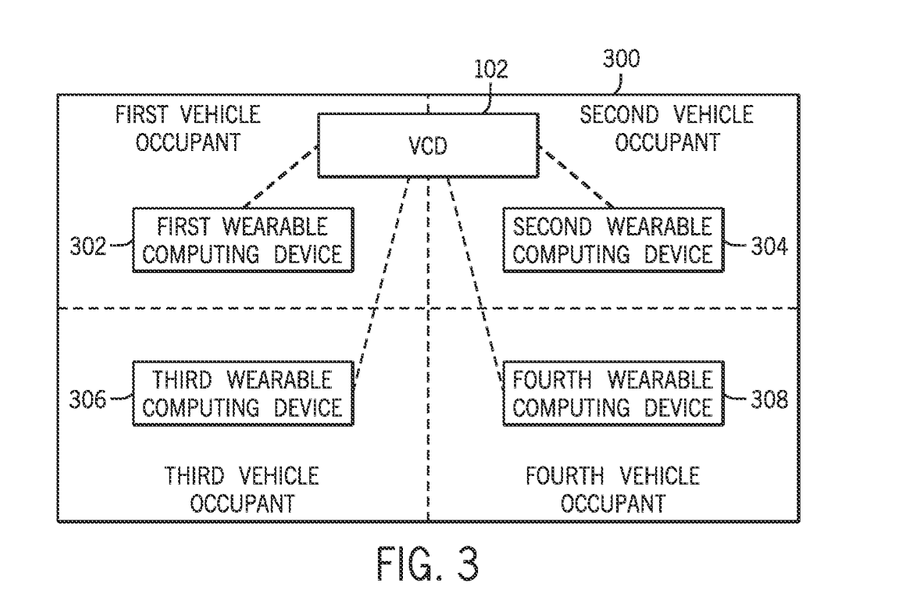
FIG. 3 is a schematic diagram of a vehicle implementing a system for dynamic vehicle control affecting sleep states of vehicle occupants according to an exemplary embodiment.

Generally, the systems and methods disclosed herein provide dynamic vehicle control affecting sleep states of vehicle occupants by integrating data from wearable computing devices associated with the vehicle occupants and data from the vehicle and vehicle systems. Dynamic and customized control of the vehicle and vehicle systems can provide induced sleep states for one or more of the vehicle occupants. Referring now to the drawings, wherein the showings are for purposes of illustrating one or more exemplary embodiments and not for purposes of limiting same, FIG. 1 is a schematic diagram of an operating environment 100 for implementing systems and methods for dynamic vehicle control affecting sleep states of vehicle occupants according to an exemplary embodiment. The components of environment 100, as well as the components of other systems, hardware architectures, and software architectures discussed herein, can be combined, omitted, or organized into different architectures for various embodiments. Further, the components of the operating environment 100 can be implemented with or associated with a vehicle. For example, FIG. 3 illustrates a schematic diagram of a vehicle 300 implementing systems and methods for dynamic vehicle control affecting sleep states of vehicle occupants according to an exemplary embodiment.

In the illustrated embodiment of FIG. 1, the environment 100 includes a vehicle computing device 102 (VCD) with provisions for processing, communicating and interacting with various components of a vehicle and other components of the environment 100. In one embodiment, the VCD 102 can be implemented with the vehicle 300 (FIG. 3), for example, as part of a telematics unit, a head unit, a navigation unit, an infotainment unit, an electronic control unit, among others. In other embodiments, the VCD 102 can be implemented remotely from the vehicle 102, for example, with a portable device (not shown) or another device connected via a network (e.g., a network 126).

Generally, the VCD 102 includes a processor 104, a memory 106, a disk 108, a position determination device 110 and an input/output (I/O) interface 112, which are each operably connected for computer communication via a bus 114 and/or other wired and wireless technologies. The I/O interface 112 provides software and hardware to facilitate data input and output between the components of the VCD 102 and other components, networks, and data sources, which will be described herein. Additionally, as will be described in further detail herein, the processor 104 includes a state determination module 116, a vehicle control module 118 and a state monitoring module 120, each suitable for providing dynamic vehicle control affecting sleep states of vehicle occupants facilitated by the components of the environment 100.

Figure 2:
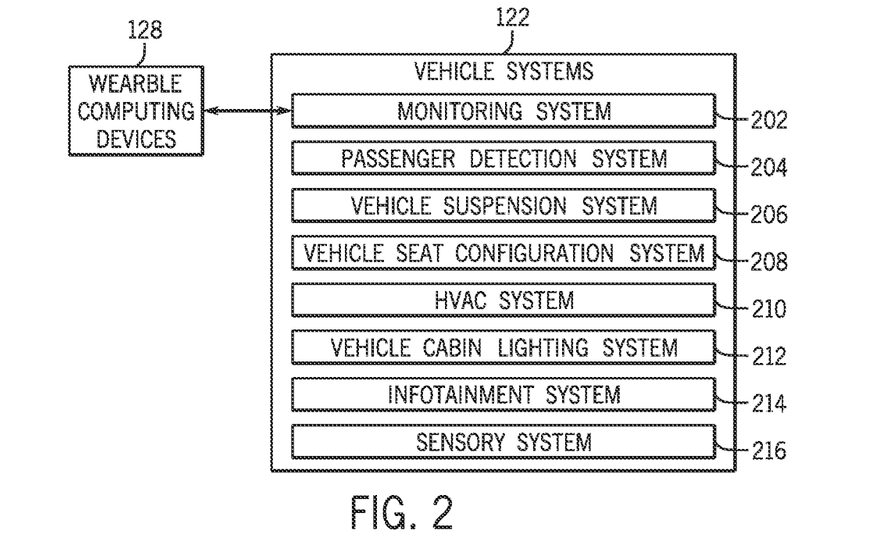
FIG. 2 is a schematic diagram of vehicle systems according to an exemplary embodiment.

The VCD 102 is also operably connected for computer communication (e.g., via the bus 114 and/or the I/O interface 112) to one or more vehicle systems 122. Vehicle systems can include, but are not limited to, any automatic or manual systems that can be used to enhance the vehicle, driving, and/or safety. FIG. 2 illustrates vehicle systems 122 according to an exemplary embodiment. It is understood that the vehicle systems shown in FIG. 2 are exemplary in nature and other vehicle systems can be implemented with the systems and methods discussed herein. In the embodiment shown in FIG. 2, the vehicle systems 122 can include a monitoring system 202. The monitoring system 202 can include various sensors (e.g., vehicle sensors 124) for monitoring one or more vehicle occupants, and in particular, monitoring physiological data of the one or more vehicle occupants, which will be discussed in further detail below. In one embodiment, which will also be discussed in further detail below, the monitoring system 202 can be operably connected for computer communication to one or more wearable computing devices 128.

The vehicle systems 122 can also include a passenger detection system 204. The passenger detection system 204 detects the presence of a vehicle occupant in a vehicle seat in an active or passive manner. For example, the passenger detection system 204 can use vehicle seat sensors, seat-belt sensors, imaging devices, among other technologies, to detect the presence of a vehicle occupant. Further, in some embodiments, which will be discussed herein, the passenger detection system 204 can classify a vehicle occupant in a vehicle seat as a type of vehicle occupant (e.g., an adult, a child, an infant, a pet). The vehicle systems 122 can also include a vehicle suspension system 206 that manages a relative motion between the vehicle and its wheels to provide proper road handling, safety and vehicle occupant comfort. For example, the vehicle suspension system 206 can generally include and control, springs, shocks, struts between the vehicle and its wheels.

The vehicle systems 122 can also include a vehicle seat configuration system 208 that controls parameters of each vehicle seat in the vehicle. For example, the vehicle seat configuration system 208 can control vehicle seat position (e.g., recline, head support, location), vehicle seat cushion settings (e.g., firmness, bolstering), vehicle seat temperature (e.g., seat cooling/heating) and vehicle seat tactile stimulation (e.g., vibration, massage), among others. The vehicle systems 122 can also include a climate control system (e.g., HVAC) system 210 that controls air temperature, air direction, air flow in different locations of the vehicle. Further, the vehicle systems 122 can include a vehicle cabin lighting system 212 to control interior vehicle cabin lights (e.g., color, shades, intensity, dimming) in different locations of the vehicle.

The vehicle systems 122 can also include an infotainment system (e.g., audio/visual media system) 214 that controls audio (e.g., audio content, volume, white noise, sound bubble) and visual media (e.g., video content, visual stimulation) in different locations of the vehicle. Further, the vehicle systems 122 can include a sensory system 216 that can supply scents to different areas of the vehicle.

Referring again to FIG. 1, and as mentioned above, the vehicle systems 122 include and/or are operably connected for computer communication to various vehicle sensors 124. It is understood that sensors (e.g., vehicle sensors 124, sensors of the wearable computing devices 128), as discussed herein, can be any type of sensor, for example, acoustic, electric, environmental, optical, imaging, light, pressure, force, thermal, temperature, proximity, among others. The vehicle sensors 124 provide and/or sense information associated with one or more vehicle occupants (e.g., via the monitoring system 202 of FIG. 2), the vehicle, the vehicle environment, and/or the vehicle systems 122. It is understood that the vehicle sensors can include, but are not limited to, the vehicle sensors 124 associated with the vehicle systems 122 and other vehicle sensors associated with the vehicle. Specific vehicle system sensors can include, but are not limited to, vehicle speed sensors, accelerator pedal sensors, brake sensors, throttle position sensors, wheel sensors, anti-lock brake sensors, camshaft sensors, among others. Other vehicle sensors can include, but are not limited to, cameras mounted to the interior or exterior of the vehicle, radar and laser sensors mounted to the exterior of the vehicle, external cameras, radar and laser sensors (e.g., on other vehicles in a vehicle-to-vehicle network, street cameras, surveillance cameras).

As mentioned above, the vehicle sensors 124 are operable to sense a measurement of data associated with the vehicle, the vehicle environment (e.g., interior, exterior), the vehicle systems 122, and/or vehicle occupants of the vehicle, and generate a data signal indicating said measurement of data. These data signals can be converted into other data formats (e.g., numerical) and/or used by the vehicle systems 122 and/or the VCD 102 to generate other data metrics and parameters.

The VCD 102 is also operatively connected for computer communication to the network 126 and wearable computing devices 128. It is understood that the connection from the I/O interface 112 to the network 126 and the wearable computing devices 128 can be facilitated in various ways. For example, through a network connection (e.g., wired or wireless), a cellular data network from a portable device (not shown) or a wearable computing device 128, a vehicle to vehicle ad-hoc network (not shown), an in-vehicle network (not shown), among others.

The network 126 is, for example, a data network, the Internet, a wide area network or a local area network. The network 126 serves as a communication medium to various remote devices (e.g., databases, web servers, remote servers, application servers, intermediary servers, client machines, other portable devices). It is understood that in some embodiments, the one or more wearable computing devices 128 can be included in the network 126, accessed by the VCD 102 through the network 126, and/or the network 126 can access the wearable computing devices 128. Thus, in some embodiments, the VCD 102 can obtain data from the wearable computing devices 128 via the network 126.

As mentioned above, the wearable computing devices 128 generally provide data to the VCD 102, the data being associated with the user wearing or associated with the wearable device 128. As discussed above, it is understood that the wearable devices 128 can include, but are not limited to, a computing device component (e.g., a processor) with circuitry that can be worn or attached to user. In some embodiments, the wearable devices 128 can be a portable device (e.g., a mobile device, a portable medical device).

The wearable devices 128 as connected to a vehicle are illustrated in FIG. 3, which illustrates a schematic diagram of a vehicle implementing a system for dynamic vehicle control affecting sleep states of vehicle occupants according to an exemplary embodiment. The vehicle 300 can include the VCD 102 of FIG. 1. As shown in FIG. 3, the system and methods described herein can include one or more wearable computing devices that are each operably connected for computer communication to the VCD 102. For example, in FIG. 3, the VCD 102 is operably connected for computer communication to a first wearable computing device 302, associated with a first vehicle occupant; a second wearable computing device 304 associated with a second vehicle occupant; a third wearable computing device 306 associated with a third vehicle occupant; and a fourth wearable computing device 308 associated with a fourth vehicle occupant. It is understood that the systems and methods disclosed herein can include any number of vehicle occupants and wearable computing devices. Further, in some embodiments, the wearable computing device can include a device ID, which can be transmitted and/or accessed from the wearable computing device to the VCD 102 and used by the VCD 102 to identify the vehicle occupant associated with the wearable computing device.

Figure 4:
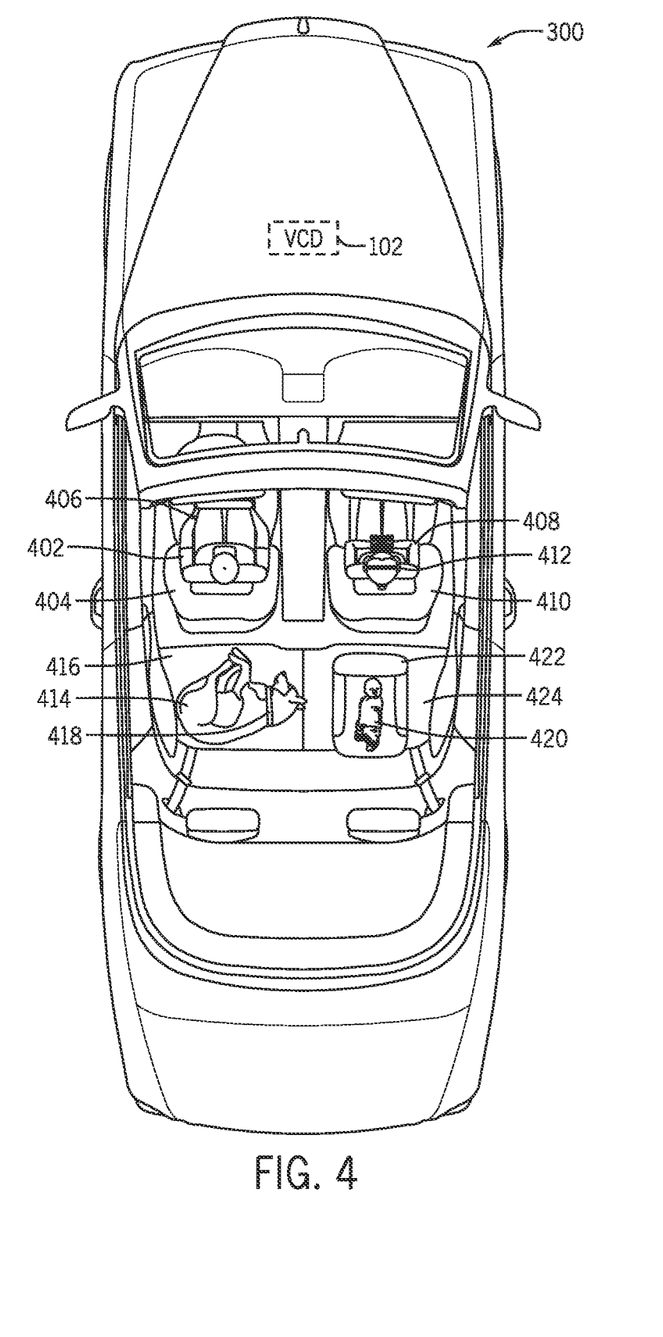
FIG. 4 is a schematic view of the vehicle of FIG. 3 including an illustrative example of vehicle occupants, the vehicle implementing a system for dynamic vehicle control affecting sleep states of the vehicle occupants according to an exemplary embodiment.

Referring now to FIG. 4, an illustrative example of the vehicle of FIG. 3 is shown including an illustrative example of vehicle occupants and wearable computing devices connected to the VCD 102. As shown in FIG. 4, a first vehicle occupant 402 is seated in a vehicle seat 404. The first vehicle occupant 402 is associated with a first wearable computing device 406, a wristband. The second vehicle occupant 408 is seated in a vehicle seat 410. The second vehicle occupant 408 is associated with a second wearable computing device 412, a head band. A third vehicle occupant 414, a dog, is positioned in a vehicle seat 416. The third vehicle occupant 414 is associated with a third wearable computing device 418, a collar. Further, a fourth vehicle occupant 420, a baby (e.g., an infant), is seated in a baby car seat 422, the baby car seat coupled to a vehicle seat 424. In this embodiment, the baby car seat 422 can be the fourth wearable computing device. In another embodiment, a blanket (not shown) covering the baby could be the fourth wearable computing device. It is understood that FIG. 4 is exemplary in nature and any number of vehicle occupants, any type of vehicle occupants, and any type of wearable computing device can be implemented.

Referring again to FIG. 1, system shown will now be described in operation according to an exemplary embodiment. As discussed above with FIGS. 1 and 3, system includes a wearable computing device 128 associated with a vehicle occupant (e.g., the vehicle occupants shown in FIG. 3). The methods and systems described herein will refer to a wearable computing device 128 and a vehicle occupant, however, it is appreciated that any number of wearable computing devices and vehicle occupants can be implemented. Further, the system includes a vehicle with a vehicle system, vehicle sensors and a processor. For example, as discussed above, the vehicle 300 of FIG. 3, can include one or more vehicle systems 122 and one or more vehicle sensors 124. The vehicle 300 and in particular, the VCD 102 includes the processor 104. The processor 104 is operably connected for computer communication to the wearable computing device 128.

In operation, the state determination module 116 of the processor 104 determines a state of the vehicle occupant based on physiological data. The term "state of the vehicle occupant" can refer to a physiological state of the vehicle occupant. In some embodiments, the state of the vehicle occupant can refer to a state of relaxation, a sleeping state, a state of drowsiness, a sleep cycle state, among others. In some embodiments, the state of the vehicle occupant is a numerical value or other kind of value for distinguishing between two or more physiological states. For example, the state of the vehicle occupant can be given as a percentage, a value between 1 and 10, a non-numerical value, a discrete state, a discrete value, a continuous value, among others.

The state of the vehicle occupant is based on at least physiological data. Physiological data can include, but is not limited to, heart information, such as, heart rate, heart rate pattern, blood pressure, oxygen content, among others. Physiological data can also include brain information, such as, electroencephalogram (EEG) measurements, functional near infrared spectroscopy (fNIRS), functional magnetic resonance imaging (fMRI), among others. Physiological data can also include digestion information, respiration rate information, salivation information, perspiration information, pupil dilation information, body temperature, muscle strain, as well as other kinds of information related to the autonomic nervous system or other biological systems of the vehicle occupant. In some embodiments, physiological data can also include behavioral data, for example, mouth movements, facial movements, facial recognition, head movements, body movements, hand postures, hand placement, body posture, gesture recognition, among others.

The VCD 102 can receive and/or access the physiological data from different sources. In one embodiment, the state determination module 116 determines a state of the vehicle occupant based on physiological data received from at least one of the wearable computing device 128 and the vehicle (e.g., the vehicle systems 122 and/or the vehicle sensors 124). For example, the wearable device 128 can include sensors for sensing and determining various parameters of a user, that can include location, motion, and physiological parameters, among others. In one embodiment, the sensors include bio-sensors for sensing physiological data and other data associated with the body and biological system of the associated vehicle occupant. Additionally, it is appreciated that some physiological data can be sensed and/or determined by the one or more wearable devices 128 using gesture tracking and/or recognition implemented by the wearable devices 128.

Further, the monitoring system 202 of FIG. 2 can sense and determine physiological data of one or more vehicle occupants. For example, the monitoring system 202 can include one or more bio-monitoring sensors, heart rate sensors, blood pressure sensors, oxygen content sensors, respiratory sensors, perspiration sensors, imaging sensors to sense eye movement, pupil dilation, gestures, as well as any other kinds of sensors for monitoring one or more vehicle occupants (e.g., vehicle sensors 124). It is understood that said sensors of the monitoring system 202 could be disposed in any location of a vehicle (e.g., the vehicle 300, FIG. 3). For example, sensors could be disposed in a steering wheel, seat, armrest or other component to detect physiological data associated with the one or more vehicle occupants.

It is understood that physiological data can be obtained from both the wearable computing devices 128 and the monitoring system 202 as shown in FIG. 2. Further, the physiological data from both the wearable computing devices 128 and/or the monitoring system 202 can be received in real time or stored and aggregated at the wearable device 128, the monitoring system 202 and/or a remote server accessed through the network 124. It is understood that the one or more wearable devices 128 and/or the monitoring system 202 can obtain other types of data associated with the user by accessing local or remotely stored data or data through a network connection (e.g., the network 126). For example, the wearable devices 128 can include data on other inputs a vehicle occupant encounters on a daily basis (e.g., calendar schedules, social media information).

Referring again to the operation of the system shown in FIG. 1, the state determination module 116 can determine a target sleep state of the vehicle occupant based on at least one of the state of the vehicle occupant, the physiological data and vehicle system data. The term "target sleep state" can refer to a future (i.e., target) physiological state for a vehicle occupant, for example, a state of relaxation, a sleeping state, a state of drowsiness, a sleep cycle state, among others. In some embodiments, the target sleep state is a numerical or other kind of value for distinguishing between two or more physiological states. For example, the target sleep state can be given as a percentage, a value between 1 and 10, a non-numerical value, a discrete state, a discrete value, a continuous value, among others. In some embodiments, the target sleep state is an increased state of sleepiness in relation to the state of the vehicle occupant.

As mentioned above, the target sleep state can be determined by the state determination module 116 based on at least one of the state of the vehicle occupant (discussed above), the physiological data (discussed above) and vehicle system data. The vehicle system data can be received from the one or more vehicle systems 122 and/or the vehicle sensors 124. For example, the VCD 102 can receive vehicle system data from the vehicle systems 122 and/or the vehicle sensors 124. Vehicle system data can include information related to the vehicle 300 of FIG. 3 and/or the vehicle systems 122 of FIG. 2. Exemplary vehicle system data includes, but is not limited to, steering data, lane departure data, blind spot monitoring data, braking data, collision warning data, navigation data (e.g., from the position determination device 110), collision mitigation data, auto cruise control data, vehicle model, vehicle make, vehicle identification number. Vehicle system data can be obtained by the VCD 102, the vehicle systems 122 and/or the vehicle sensors 124.

In one embodiment, the target sleep state can be determined by the state determination module 116 based on a sleep mode received from the wearable computing device 128 or the vehicle 300 (e.g., the vehicle systems 122). For example, a vehicle occupant can set a sleep mode on the wearable computing device 128 and the wearable computing device 128 can transmit the sleep mode to the state determination module 116. As an illustrative example, if the vehicle occupant wishes to fall asleep, the vehicle occupant can set a sleep mode on the wearable computing device 128. The state determination module 116, upon receiving the sleep mode input from the wearable computing device 128, can set the target sleep state to a state of sleep based on the sleep mode input. As another illustrative example, a vehicle occupant in the vehicle can provide a user input indicating a desire to sleep. For example, the vehicle occupant can state an utterance "I want to sleep." The infotainment system 214 can receive the utterance through the infotainment system 214 (e.g., via audio sensors/microphones in the vehicle) and determine a sleep mode from the utterance by utilizing speech recognition.

The state determination module 116 can also determine physical characteristics of the vehicle occupant. The physical characteristics can be used to determine a state of the vehicle occupant, a target sleep state of the vehicle occupant and/or used to control on or more vehicle systems, which will be described in further detain herein. Physical characteristics can include, but are not limited to, build characteristics (e.g., stocky, overweight, obese, skinny, trim), height characteristics (e.g., short, tall, average), age, and gender.

Data about physical characteristics can be received by the VCD 102 from the wearable computing device 128 and/or the vehicle systems 122. Alternatively, data about physical characteristics can be determined based on physiological data and/or received from a vehicle occupant profile (not shown). The vehicle occupant profile can be stored at the wearable device 128 and/or the VCD 102. Additionally, in some embodiments, the state determination module 116 can determine a vehicle occupant type of the vehicle occupant. The vehicle occupant type can be at least one of an adult, a teen, a child, an infant, and a pet. In one embodiment, the vehicle occupant type is based on data from a passenger detection system, for example, the passenger detection system 204 of FIG. 2. The vehicle occupant type can also be determined based on physical characteristics data or data from the vehicle occupant profile.

Referring now to FIG. 4, illustrative examples of physical characteristics and vehicle occupant types will be described. In this embodiment, the first vehicle occupant 402 is classified as vehicle occupant type adult. Physical characteristics of the first vehicle occupant 402 can include gender (e.g., male), age (e.g., 42), height (e.g., 6'), weight (e.g., 200 lbs). The second vehicle occupant 408 is classified as vehicle occupant type adult. Physical characteristics of the second vehicle occupant 108 can include gender (female), age (e.g., 20), height (e.g., 5'5"), weight (e.g., 120 lbs). The third vehicle occupant 414 is classified as vehicle occupant type pet. Physical characteristics of the third vehicle occupant 414 can include type (e.g., dog), species (e.g., Siberian husky), age (e.g., 5), weight (e.g., 80 lbs). Further, the fourth vehicle occupant 420 is classified as vehicle occupant type infant. Physical characteristics of the fourth vehicle occupant 420 can include gender (e.g., female), age (e.g., 10 months), height (e.g., 7"), weight (e.g., 15 lbs).

Referring again to the operation of the system shown in FIG. 1, the vehicle control module 118 controls the vehicle systems 122 based on the state of the vehicle occupant in relation to the target sleep state. By controlling the vehicle systems 122 based on the state of the vehicle occupant in relation to the target sleep state, the target sleep state can be induced in the vehicle occupant. In some embodiments, the vehicle control module 118 controls the vehicle systems 122 based on the vehicle occupant type and the state of the vehicle occupant in relation to the target sleep state. In other embodiments, the vehicle control module 118 controls the vehicle systems 122 based on user preferences, for example, stored in the vehicle occupant profile. It is understood that the vehicle control module can control more than one vehicle system and/or more than one parameter of the vehicle systems.

As an illustrative example, the vehicle control module 118 can control vehicle systems 122 by changing and/or setting a parameter of the one or more vehicle systems 118. For example, the vehicle control module 118 can change a parameter of a vehicle suspension system 206 in relation to the vehicle occupant to induce the target sleep state (e.g., soften the vehicle suspension system 206 in a location affecting the vehicle occupant). As another example, the vehicle control module 118 can change a parameter of a vehicle seat configuration system 206 to the vehicle occupant to induce the target sleep state. For example, a parameter of the vehicle seat configuration can be a firmness parameter of the vehicle seat occupied by the vehicle occupant.

Referring again to the operation of system shown in FIG. 1, the state monitoring module 120 monitors the state of the vehicle occupant including monitoring the physiological data of the vehicle occupant in response to controlling the vehicle systems. In some embodiments, the state monitoring module 120 can receive physiological data and determine an updated state of the vehicle occupant based on the physiological data. The state monitoring module 120 can transmit a command to the vehicle control module 118 to control the vehicle systems 122 according to the monitoring in relation to the target sleep state. For example, the vehicle control module 118 can change a different parameter of the vehicle system and/or change a parameter of another vehicle system. Accordingly, by monitoring the vehicle occupants, dynamic and customized control of the vehicle and vehicle systems can provide induced sleep states for one or more of the vehicle occupants. The operation of the system shown in FIG. 1 will now be discussed in further detail in accordance with exemplary methods.

II. Exemplary Methods

Figure 5:
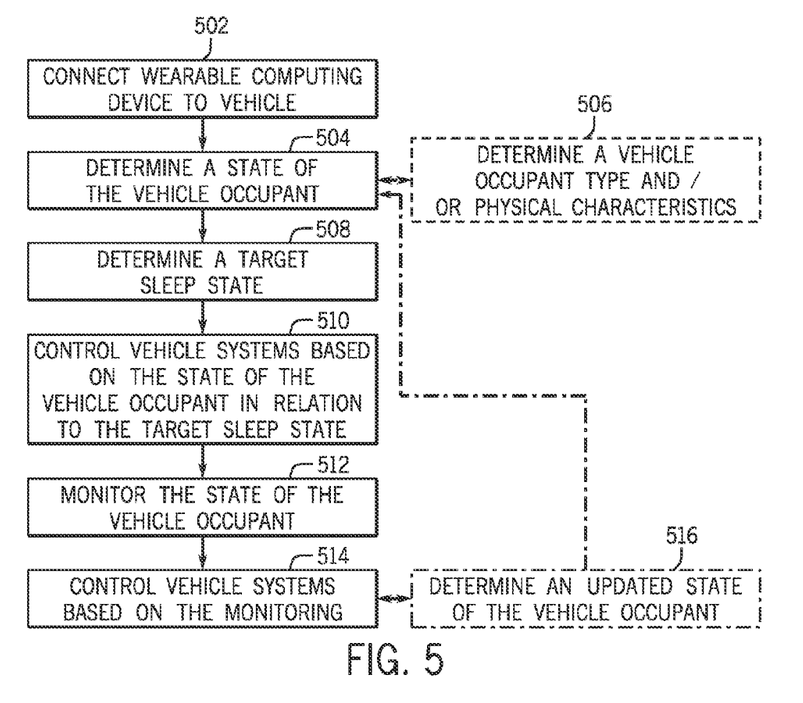
FIG. 5 is a process flow diagram of a method for dynamic vehicle control affecting sleep states of vehicle occupants according to an exemplary embodiment.

Referring now to FIG. 5, a method for dynamic vehicle control affecting sleep states of vehicle occupants according to an exemplary embodiment will be described. FIG. 5 will be described with reference to the components of FIGS. 1-4. At block 502, the method includes connecting a wearable computing device associated with a vehicle occupant to a vehicle. In one embodiment, the VCD 102 detects the presence of one or more wearable computing devices 128 located in the vehicle and initiates an operable connection from the VCD 102 to the wearable computing device 128 for computer communication. In other embodiments, the wearable computing device 128 can automatically connect to the VCD 102 for computer communication. The connection can be facilitated by various wired and wireless technologies, for example, near field communication, Bluetooth, WiFi, wired dongles, among others. Connection between the wearable computing device and the VCD 102 allows for bi-directional computer communication between the wearable computing devices and the VCD 102. FIG. 3 illustrates a vehicle 300 showing one or more wearable computing devices that are each operably connected for computer communication to the VCD 102 according to an exemplary embodiment.

Referring again to the method of FIG. 5, at block 504, the method includes determining a state of the vehicle occupant based on physiological data received from at least one of the wearable computing device and the vehicle. As discussed above, the state of the vehicle occupant can refer to a physiological state of the vehicle occupant. In some embodiments, the state of the vehicle occupant can refer to a state of relaxation, a sleeping state, a state of drowsiness, a sleep cycle state, among others. The state determination module 116 can determine the state of the vehicle occupant based on physiological data received from the wearable computing devices 128 and/or received from the vehicle systems 122 and the vehicle sensors 124, for example, from the monitoring system 202.

In one embodiment, at block 506, the method includes determining a vehicle occupant type of the vehicle occupant. The vehicle occupant type is at least one of an adult, a teen, a child, an infant, and a pet. In one embodiment, the state determination module 116 determines the vehicle occupant type based on the physiological data received at block 504. In another embodiment, the vehicle occupant type is determined by a passenger detection system 204. The passenger detection system 204 can include various sensors (e.g., vehicle sensors 124, seat belt sensors, weight sensors in the vehicle seats, among others) to determine a vehicle occupant type.

The method at block 506 can also include determining one or more physical characteristics of the vehicle occupant based on at least one of the physiological data and a vehicle occupant profile. In one embodiment, the state determination module 116 determines one or more physical characteristics of the vehicle occupant. As discussed above, physical characteristics can include, but are not limited to, build characteristics (e.g., stocky, overweight, obese, skinny, trim), height characteristics (e.g., short, tall, average), age, and gender. The vehicle occupant profile (not shown) can be stored at the one or more wearable computing devices 128 and/or the VCD 102 (e.g., the memory 106 and/or the disk 108). The vehicle occupant profile can also include user preferences related to the one or more vehicle systems. Further, the vehicle occupant profile can be associated with a vehicle occupant ID and/or a wearable computing device ID associated with the particular vehicle occupant. The vehicle occupant ID and/or wearable computing device ID can be used for vehicle occupant identification and to determine the vehicle occupant associated with a particular the wearable computing device.

Referring again to the method of FIG. 5, at block 508, the method includes determining a target sleep state of the vehicle occupant based on at least one of the state of the vehicle occupant, the physiological data, and vehicle system data. As discussed above, the vehicle system data is received from the vehicle systems 122 and/or the vehicle sensors 124 of the vehicle. As discussed above, a target sleep state can refer to a future (e.g., a target) physiological state for a vehicle occupant, for example, a state of relaxation, a sleeping state, a state of drowsiness, a sleep cycle state, among others. In one embodiment, the target sleep state is an increased state of sleepiness in relation to the state of the vehicle occupant. In another embodiment, the target sleep state is based on a length of a vehicle trip received from the vehicle. For example, the state determination module 116 can receive vehicle trip information from the position determination device 110. The value of the target sleep state can be a function of the length of the vehicle trip. Thus, for a long vehicle trip, the target sleep state can be determined as a deep sleep, while for a short vehicle trip, the target sleep state can be determined as a state of light relaxation.

At block 510, the method includes controlling a vehicle system of the vehicle based on the state of the vehicle occupant in relation to the target sleep state. Thus, control of the one or more vehicle systems induces the target sleep state. For example, in one embodiment, the target sleep state is an increased state of sleepiness in relation to the state of the vehicle occupant and controlling the vehicle systems of the vehicle based on the sleep state in relation to the target sleep state induces the increased state of sleepiness.

In one embodiment, the vehicle control module 118 controls the vehicles system of the vehicle based on the state of the vehicle occupant in relation to the target sleep state. For example, the vehicle control module 118 can receive vehicle system data from the vehicle systems 122, identify a parameter of the one or more vehicle systems 122, and modify the parameter to induce the target sleep state. In one embodiment, the vehicle control module 118 determines the vehicle systems and/or the parameters of the vehicle systems to control and/or modify based on user preferences from a vehicle occupant profile. In other embodiments, the vehicle control module 118 determines the vehicle systems and/or the parameters of the vehicle systems to control and/or modify based on historical data stored for a particular vehicle occupant. For example, pattern recognition and machine learning can be used to determine the vehicle systems and/or the parameters of the vehicle systems to control and/or modify for a particular vehicle occupant. In another embodiment, controlling the one or more vehicle systems is based on the vehicle occupant type and one or more physical characteristics of the vehicle occupant as determined at block 506.

At block 512, the method includes monitoring the state of the vehicle occupant including monitoring the physiological data of the vehicle occupant in response to controlling the vehicle system. For example, the state monitoring module 120 can continue to receive and monitor physiological data as described above at block 504. For example, the monitoring system 202 and the wearable devices 128 can continue to sense and receive physiological data associated with the one or more vehicle occupants. The physiological data can indicate whether the state of the vehicle occupant has changed in response to controlling the one or more vehicle systems. In one embodiment, at block 516, monitoring the state of the vehicle occupant includes determining an updated state of the vehicle occupant, for example, as described at block 504. Further, at block 514, the method includes controlling the vehicle system according to the monitoring in relation to the target sleep state.

Figure 6:
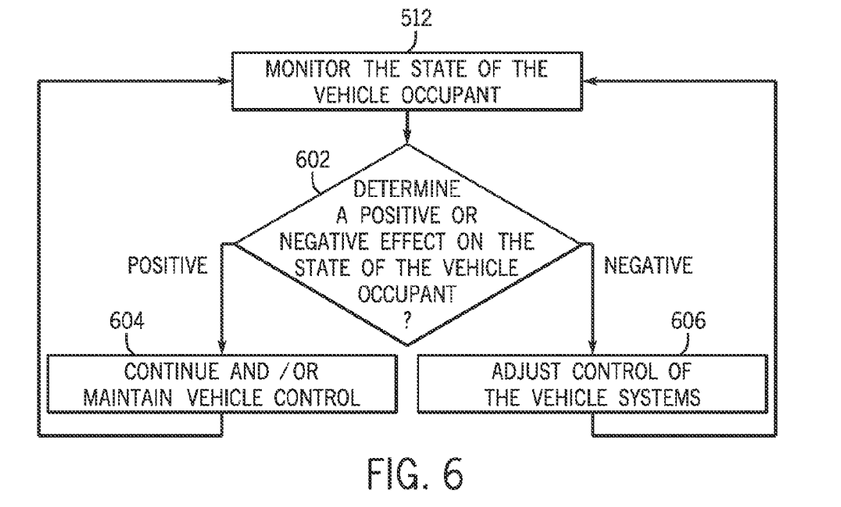
FIG. 6 is a process flow diagram of a process for monitoring the state of the vehicle occupant of the method of FIG. 5.

Monitoring the state of the vehicle occupant as discussed at blocks 512, 514 and 516 is described in more detail with reference to FIG. 6. In one embodiment, at block 602, monitoring the state of the vehicle occupant includes determining a positive or negative effect on the state of the vehicle occupant in relation to the target sleep state. For example, the state monitoring module 120 can determine the positive or negative effect on the state of the vehicle occupant in relation to the target sleep state based on monitoring the physiological data and/or based on the updated state of the vehicle occupant. If the physiological data and/or the updated state of the vehicle occupant indicate the state of the vehicle occupant is reaching or is at the target state of the vehicle occupant, a positive effect has occurred. For example, in one embodiment, the state monitoring module 120 can calculate a difference between the updated state of the vehicle occupant and the target sleep state. If the difference between the updated state of the vehicle occupant and the target sleep state is less than the difference between the state of the vehicle occupant and the target sleep state, then a positive effect has occurred.

As an illustrative example, if the state of the vehicle occupant is a light sleep state, the target state of the vehicle occupant is a deep sleep state, and the physiological data and/or the updated state of the vehicle occupant is determined to indicate a medium sleep state, a positive effect has occurred. Accordingly, if a positive effect is determined at block 602, the method includes at block 604 continuing and/or maintaining control the vehicle system.

Referring again to block 602, a negative effect on the state of the vehicle occupant can be determined. For example, in one embodiment, the state monitoring module 120 can calculate a difference between the updated state of the vehicle occupant and the target sleep state. If the difference between the updated state of the vehicle occupant and the target sleep state is more than the difference between the state of the vehicle occupant and the target sleep state, then a negative effect has occurred. Said differently, if the physiological data and/or the updated state of the vehicle occupant indicate the state of the vehicle occupant is moving away from the target sleep state, a negative effect has occurred. As an illustrative example, if the state of the vehicle occupant is a light sleep state, the target state of the vehicle occupant is a deep sleep state, and the physiological data and/or the updated state of the vehicle occupant is determined to indicate an awake state, a negative effect has occurred.

Accordingly, if a negative effect is determined at block 602, the method includes at block 606, adjusting control of the vehicle system. For example, upon determining a negative effect on the state of the vehicle occupant in relation to the target sleep state, controlling the one or more vehicle systems further includes controlling a different vehicle system. In another embodiment, upon determining a negative effect on the state of the vehicle occupant in relation to the target sleep state, controlling a different parameter of the vehicle system and/or adjusting a parameter of the vehicle system.

In one embodiment, the determination made at block 602 can be stored for pattern recognition and machine learning. For example, a vehicle occupant ID, a state of the vehicle occupant, a target sleep state, a vehicle system and/or parameter controlled and an effect on the state of the vehicle occupant can be stored at a database and/or memory (e.g., the memory 106, the disk 108, a remote server via the network 126 and/or at the wearable computing device 128). This information can be used by the vehicle control module 118 and the state monitoring module 120 to determine the target sleep state and determine which vehicle system and/or parameters of the vehicle system to control in order to induce the target sleep state. Accordingly, the systems and methods described herein allow for dynamic and customized control of a vehicle and vehicle systems to induced sleep states for one or more of the vehicle occupants. Illustrative examples of the systems and methods described herein will now be discussed.

III. Illustrative Examples

Illustrative examples of the systems and methods discussed in FIGS. 1-6 will now be described. It is understood that these illustrative examples are exemplary in nature and other examples can be realized. Illustrative examples of provide dynamic vehicle control affecting sleep states of vehicle occupants will be described with respect to the vehicle occupants shown in FIG. 4. As discussed above, the wearable computing devices associated with each vehicle occupant are connected to the vehicle 300, for example, to the VCD 102. As discussed above, the state determination module 116 determines a state of the vehicle occupant based on physiological data received from at least one of the wearable computing device and the vehicle. Regarding physiological data received from the vehicle, the monitoring system 222 can include various vehicle sensors 126 for sensing physiological data for each vehicle occupant. For example, vehicle sensors 126 can be included in various locations of the vehicle 300 and in various locations of each vehicle seat 404, 410, 416, and 424.

As discussed above, the state determination module 116 determines a target sleep state of the vehicle occupant based on at least one of the state of the vehicle occupant, the physiological data, and vehicle system data. In some embodiments, the target sleep state is based on physiological characteristics and/or a vehicle occupant profile. For example, it can be determined that the first vehicle occupant 402 is in an awake state. Based on vehicle trip information received from the position determination device 110 (e.g., a length of the vehicle trip, a destination) and calendar information from the first wearable computing device 406 associated with the first vehicle occupant 402, the state determination module 116 can determine that the length of the vehicle trip is 40 minutes and the first vehicle occupant 402 must complete a task at the end of the vehicle trip according to the calendar information. Accordingly, the state determination module 116 can set a target sleep state for the first vehicle occupant 402 to a state of medium relaxation so the first vehicle occupant 402 can enjoy the long vehicle trip and be prepared to complete said task at the end of the trip.

As another illustrative example, it can be determine that the second vehicle occupant 408 is in a light sleep state. Based on vehicle trip information received from the position determination device 110 (e.g., a length of the vehicle trip, a destination) and blood sugar information (e.g., physiological data) from the second wearable computing device 412, the state determination module 116 can determine the length of the vehicle trip is long and the second vehicle occupant 408 has recently eaten a large meal (e.g., based on the blood sugar information). Accordingly, the state determination module 116 can set a target sleep state for the second vehicle occupant 408 to a state of medium sleep.

As a further illustrative example, it can be determined that the fourth vehicle occupant 420 is in an awake state. Based on vehicle trip information received from the position determination device 110 (e.g., a length of the vehicle trip, a destination) and physical characteristics (e.g., the fourth vehicle occupant 420 is an infant), the state determination module 116 can set a target sleep state for the fourth vehicle occupant 420 to a state of deep sleep.

As discussed above, the vehicle control module 118 controls a vehicle system of the vehicle based on the state of the vehicle occupant in relation to the target sleep state. The vehicle control module 118 can also control the vehicle system of the vehicle based on the vehicle occupant type and one or more physical characteristics of the vehicle occupant. Accordingly, referring to the illustrative example above of the first vehicle occupant 402, the vehicle control module 118 can control the position of the vehicle seat 404, via the vehicle seat configuration system 208, to a slightly reclined position and control interior cabin lights around the first vehicle occupant 402 to a dimmed setting via the vehicle cabin lighting system, to induce the target sleep state of a state of medium relaxation. The vehicle control module 118 can determine which vehicle systems and/or parameters to control based on a vehicle occupant profile associated with the first vehicle occupant, machine learning (e.g., by querying a database), and/or based on the vehicle occupant type, physiological data, vehicle system data, among others.

Referring to the illustrative example above of the second vehicle occupant 408, the vehicle control module 118 can control the position of the vehicle seat 410, via the vehicle seat configuration system 208, to a fully reclined position and control the infotainment system 214 to play relaxing music in an area around the second vehicle occupant 408, to induce the target sleep state of a state of medium sleep.

Further, referring to the illustrative example above of the fourth vehicle occupant 420, the vehicle control module 118 can control the vehicle suspension system 206 to soften suspension in an area under the fourth vehicle occupant 420, control the vehicle seat 422, via the seat configuration system 208, to vibrate in a steady motion, and control the infotainment system 214 to create a sound bubble around the fourth vehicle occupant 420, to induce the target sleep state of a state of deep sleep.

As discussed above, the vehicle control module 118 monitors the state of the vehicle occupant including monitoring the physiological data of the vehicle occupant in response to controlling the vehicle system. The vehicle control module 118 also controls the vehicle system according to the monitoring in relation to the target sleep state. Accordingly, referring to the illustrative example above of the first vehicle occupant 402, the vehicle control module 118 can determine an updated state of the vehicle occupant based on physiological data. In this example, vehicle control module 118 can determine an updated state of the vehicle occupant as a state of light relaxation.

Accordingly, the vehicle control module 118 can calculate a difference between the updated state of the first vehicle occupant (i.e., a state of light relaxation) and the target sleep state of the first vehicle occupant (i.e., a state of medium relaxation) and a difference between the state of the first vehicle occupant (i.e., an awake state) and the target sleep state of the first vehicle occupant (i.e., a state of medium relaxation). Here, the vehicle control module 118 determines the difference between the updated state of the vehicle occupant and the target sleep state is less than the difference between the state of the vehicle occupant and the target sleep state. Thus, a positive effect on the state of the first vehicle occupant in relation to the target state of the first vehicle occupant has occurred. Accordingly, the vehicle control module 118 can maintain and/or continue control of the vehicle systems.

Referring to the illustrative example above of the second vehicle occupant 408, the vehicle control module 118 can determine an updated state of the vehicle occupant 408 based on physiological data. In this example, vehicle control module 118 can determine an updated state of the second vehicle occupant as a state of deep sleep. Here, the vehicle control module 118 determines the difference between the updated state of the vehicle occupant and the target sleep state is more than the difference between the state of the vehicle occupant and the target sleep state. Thus, a negative effect on the state of the second vehicle occupant in relation to the target state of the second vehicle occupant has occurred. Accordingly, the vehicle control module 118 can adjust a parameter of a vehicle system and/or control a different vehicle system. For example, the vehicle control module 118 can control the position of the vehicle seat 410, via the vehicle seat configuration system 208, to a slightly reclined position instead of a fully reclined position. In another example, the vehicle control module 118 can control a different vehicle system by increasing airflow in an area around the of the second vehicle occupant 408 by controlling the HVAC system 210.

Referring to the illustrative example above of the fourth vehicle occupant 420, the vehicle control module 118 can determine an updated state of the fourth vehicle occupant 420 based on physiological data. In this example, vehicle control module 118 can determine an updated state of the second vehicle occupant as an agitated state. For example, the physiological data can indicate the fourth vehicle occupant 420 has a high body temperature, is moving often, and/or is crying. Accordingly, the vehicle control module 118 determines the difference between the updated state of the vehicle occupant and the target sleep state is more than the difference between the state of the vehicle occupant and the target sleep state. Thus, a negative effect on the state of the fourth vehicle occupant in relation to the target state of the fourth vehicle occupant has occurred. As such, the vehicle control module 118 can adjust the temperature of the air around the fourth vehicle occupant via the HVAC system 210, control the infotainment system 214 to remove the sound bubble around the fourth vehicle occupant 420 and play relaxing music around the fourth vehicle occupant 420, to induce the target sleep state of a state of deep sleep.

It is understood that upon monitoring the state of the vehicle occupant in response to controlling the vehicle system, the vehicle control module 118 can store a vehicle occupant ID, a state of the vehicle occupant, a target sleep state, a vehicle system and/or parameter controlled and an effect on the state of the vehicle occupant can be stored at a database and/or memory (e.g., the memory 106, the disk 108, a remote server via the network 126 and/or at the wearable computing device 128). This information can be used by the vehicle control module 118 and the state monitoring module 120 to determine the target sleep state and determine which vehicle system and/or parameters of the vehicle system to control in order to induce the target sleep state.

It is understood that the systems and methods described herein can continue to monitor the state of the vehicle occupant and adjust control of the vehicle systems based on the monitoring throughout a vehicle trip. Accordingly, the systems and methods described herein allow for dynamic and customized control of a vehicle and vehicle systems to induced sleep states for one or more of the vehicle occupants.

The embodiments discussed herein may also be described and implemented in the context of non-transitory computer-readable storage medium storing computer-executable instructions. Non-transitory computer-readable storage media includes computer storage media and communication media. For example, flash memory drives, digital versatile discs (DVDs), compact discs (CDs), floppy disks, and tape cassettes. Non-transitory computer-readable storage media may include volatile and nonvolatile, removable and non-removable media implemented in any method or technology for storage of information such as computer readable instructions, data structures, modules or other data. Non-transitory computer readable storage media excludes transitory and propagated data signals.

It will be appreciated that various implementations of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A computer-implemented method for dynamic vehicle control affecting sleep states of vehicle occupants, comprising:

connecting a wearable computing device associated with a vehicle occupant to a vehicle;

determining a state of the vehicle occupant based on physiological data received from at least one of the wearable computing device and the vehicle;

determining a target sleep state of the vehicle occupant based on at least one of the state of the vehicle occupant, the physiological data and vehicle system data;

controlling a vehicle system of the vehicle by transmitting a vehicle control command to the vehicle system based on the state of the vehicle occupant in relation to the target sleep state;

monitoring the state of the vehicle occupant including monitoring the physiological data of the vehicle occupant in response to controlling the vehicle system; and modifying control of the vehicle system by transmitting a second vehicle control command to the vehicle system in response to the monitoring and based on the monitored state of the vehicle occupant in relation to the target sleep state.

2. The computer-implemented method of claim 1, further including determining a vehicle occupant type of the vehicle occupant, wherein the vehicle occupant type is at least one of an adult, a teen, a child, an infant, and a pet.

3. The computer-implemented method of claim 2, further including determining one or more physical characteristics of the vehicle occupant based on at least one of the physiological data and a vehicle occupant profile.

4. The computer-implemented method of claim 3, wherein controlling the vehicle system is based on the vehicle occupant type and one or more physical characteristics of the vehicle occupant.

5. The computer-implemented method of claim 1, wherein the target sleep state is an increased state of sleepiness in relation to the state of the vehicle occupant and wherein controlling the vehicle system based on the sleep state in relation to the target sleep state induces the increased state of sleepiness.

6. The computer-implemented method of claim 1, wherein the target sleep state is based on a length of a vehicle trip received from the vehicle, wherein the value of the target sleep state is a function of the length of the vehicle trip.

7. The computer-implemented method of claim 1, wherein monitoring the state of the vehicle occupant further includes determining an updated state of the vehicle occupant.

8. The computer-implemented method of claim 1, wherein monitoring the state of the vehicle occupant further includes determining a positive or negative effect on the state of the vehicle occupant in relation to the target sleep state.

9. The computer-implemented method of claim 8, wherein upon determining a negative effect on the state of the vehicle occupant in relation to the target sleep state, controlling the vehicle system further includes controlling a different vehicle system.

10. A system for dynamic vehicle control affecting sleep states of vehicle occupants, comprising:
a wearable computing device associated with a vehicle occupant;
a vehicle including a vehicle system, vehicle sensors and a processor, the processor operably connected for computer communication to the wearable computing device;
a state determination module of the processor determines a state of the vehicle occupant based on physiological data received from at least one of the wearable computing device and the vehicle, the state determination module determines a target sleep state of the vehicle occupant based on at least one of the state of the vehicle occupant, the physiological data and vehicle system data;
a vehicle control module of the processor controls the vehicle system based on the state of the vehicle occupant in relation to the target sleep state by transmitting a vehicle control command to the vehicle system; and
a state monitoring module of the processor monitors the state of the vehicle occupant including monitoring the physiological data of the vehicle occupant after controlling the vehicle system, and the vehicle control module modifies control of the vehicle system by transmitting a second vehicle control command to the vehicle system based on the state of the vehicle occupant monitored after controlling the vehicle system in relation to the target sleep state.

11. The system of claim 10, wherein the vehicle system includes a passenger detection system, and wherein the state determination module determines a vehicle occupant type of the vehicle occupant based on vehicle data from the passenger detection system.

12. The system of claim 11, wherein the vehicle control module controls the vehicle system based on the vehicle occupant type and the state of the vehicle occupant in relation to the target sleep state.

13. The system of claim 10, wherein the state determination module determines the target sleep state as an increased state of sleepiness in relation to the state of the vehicle occupant.

14. The system of claim 10, wherein the vehicle system is a vehicle suspension system and the vehicle control module controls a parameter of the vehicle suspension system in relation to the vehicle occupant to induce the target sleep state.

15. The system of claim 10, wherein the vehicle system is a vehicle seat configuration system and the vehicle control module controls a parameter of the vehicle seat configuration system in relation to the vehicle occupant to induce the target sleep state.

16. The system of claim 15, wherein a parameter of the vehicle seat configuration system is a firmness of the vehicle seat occupied by the vehicle occupant.

17. A non-transitory computer-readable storage medium storing instructions that, when executed by a computer, causes the computer to perform a method, comprising:
connecting a wearable computing device associated with a vehicle occupant to a vehicle;
receiving physiological data associated with the vehicle occupant from at least one of the wearable computing device and the vehicle, and receiving vehicle system data from the vehicle;
determining a state of the vehicle occupant based on the physiological data and determining a target sleep state based on at least one of the state of the vehicle occupant, the physiological data and vehicle system data;
transmitting a vehicle control command to a vehicle system of the vehicle based on the state of the vehicle occupant in relation to the target sleep state;
monitoring the physiological data of the vehicle occupant in response to controlling the vehicle system and transmitting a second vehicle control command to the vehicle system in response to the monitoring, the second vehicle control command based on the monitoring in relation to the target sleep state.

18. The non-transitory computer-readable storage medium of claim 17, further including determining the vehicle control command based on the state of the vehicle occupant and vehicle data in relation to the target sleep state.

19. The non-transitory computer-readable storage medium of claim 17, wherein the targets sleep state is an increased state of sleepiness in relation to the state of the vehicle occupant.

20. The non-transitory computer-readable storage medium of claim 17, wherein monitoring the physiological data of the vehicle occupant further includes determining a positive or negative effect on the state of the vehicle occupant in relation to the target sleep state and determining the second vehicle control command based on the determination of the positive or negative effect.

* * * * *